(12) United States Patent
Omidian et al.

(10) Patent No.: US 7,056,957 B2
(45) Date of Patent: Jun. 6, 2006

(54) FORMATION OF STRONG SUPERPOROUS HYDROGELS

(75) Inventors: Hossein Omidian, Sunrise, FL (US); Jose Gutierrez-Rocca, Miami, FL (US)

(73) Assignee: KOS Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 10/827,841

(22) Filed: Apr. 20, 2004

(65) Prior Publication Data

US 2004/0224021 A1 Nov. 11, 2004

Related U.S. Application Data

(60) Provisional application No. 60/465,755, filed on Apr. 25, 2003.

(51) Int. Cl.
*C08F 8/00* (2006.01)
*C08F 8/44* (2006.01)
*C08F 251/00* (2006.01)

(52) U.S. Cl. ............... 521/99; 521/102; 521/109.1; 521/125; 521/130; 521/140; 521/142; 521/149; 521/182; 525/54.3

(58) Field of Classification Search ............ 521/99, 521/134, 102, 125, 130, 142, 149, 182, 109.1, 521/140; 525/54.3
See application file for complete search history.

(56) References Cited

U.S. PATENT DOCUMENTS 6,271,278 B1  8/2001  Park et al. ............ 521/150

2003/0232895 A1 * 12/2003 Omidian et al. ............ 521/99

OTHER PUBLICATIONS

Chen et al., "Synthesis of superporous hydrogels: hydrogels with fast swelling and superabsorbent properties," *J. Biomed. Mater. Res.*, 44(1):53-62.
Ishaug, et al., "Osteoblast function on synthetic biodegradable polymers," *J. Biomed. Mater. Res.*, 28(12):1445-1453 (1994).
Mooney, et al., "Transplantation of Hepatocytes Using Porous, Biodegradable Sponges," *Transplant Proc.*, 26(6):3425-3426 (1994).
Mooney, et al., "Biodegradable sponges for hepatocyte transplantation," *J. Biomed. Mater. Res.*, 29(8):959-965 (1995).

* cited by examiner

*Primary Examiner*—Irina S. Zemel
(74) *Attorney, Agent, or Firm*—Clark & Elbing LLP

(57) ABSTRACT

The present invention features a method for the formation of superporous hydrogels using an ion-equilibration technique. Anionic polysaccharides are included in the hydrogel reaction mixture and cations are introduced either during or after hydrogel formation. Properties of the resulting hydrogel can be subsequently adjusted by treating the cation-complexed gel with a different cation or cation mixture under equilibrating conditions. It has been found that by properly adjusting the cations and the sequence in which they are used in the equilibration process, superporous hydrogels can be formed that are highly absorbent while maintaining favorable structural properties, including strength, ruggedness, and resiliency. It has also been found that applying appropriate dehydration conditions to them after their formation can further stabilize the superporous hydrogels formed by the method of the invention.

14 Claims, No Drawings

FORMATION OF STRONG SUPERPOROUS HYDROGELS

CROSS REFERENCE TO RELATED APPLICATIONS

This application claims priority under 35 U.S.C 119 from provisional application U.S. Ser. No. 60/465,755, filed Apr. 25, 2003, the contents of which are incorporated herein by reference.

BACKGROUND OF THE INVENTION

The present invention relates to a method for the formation of superporous hydrogels having improved physical and mechanical properties.

superporous hydrogels (SPH) are chemically crosslinked hydrophilic polymers that contain a multiplicity of pores with diameters in the micrometer to millimeter range, enabling them to absorb tens of times their weight of aqueous fluids i just a fraction of a minute. SPH pores are interconnected in the hydrogel matrix such that absorbing fluid can move freely through the channels (capillaries), allowing them to swell much faster than conventional hydrogels that have the same swelling capacity.

To prepare a superporous hydrogel, a monomer, a crosslinker, a solvent (normally water), a surfactant (for foam stabilization), and a foaming aid are first mixed together, followed by the addition of an initiator. A blowing agent is then added to the mixture for the generation of gas bubbles such as, for example, the generation of caron dioxide. Once the initiator and blowing agent are added, foaming and polymerization (also refer as gelling) processes take place simultaneously. As polymerization proceeds, the viscosity of the reaction mixture increases and the bubbles being generated are trapped within the highly viscous polymer matrix. The foaming resulting from simultaneous gelation and bubble formation continues until both processed are stopped. At this stage, the product takes the form of flexible foam. To remove residual monomer, non-reacted crosslinker, and initiator impurities, the flexible foam is washed thoroughly with water. After this purification process, a water miscible alcohol such as, for example, ethanol, is added and subsequently removed to dehydrate the hydrogel. A final drying step is usually performed in an oven, preferably in a vacuum oven at low temperatures. U.S. Pat. No. 6,271,278 describes the preparation of various SPHs in detail. SPHs are also described by Chen, et al., in *J Biomed. Mater. Res.* 44:53–62 (1999).

Superporous hydrogels are generally prepared based on hydrophilic monomers, including acrylic acid and its salts, acrylamide, the potassium salt of sulfopropyl acrylate, hydroxyethyl acrylate, and hydroxyethyl methacrylate. A desirable superporous hydrogel would possess high solvent absorption properties yet be able to withstand external forces such as tension, compression, and bending. Some hydrogels have been prepared that have desirable swelling capacity and swelling rate properties. However, very high swelling superporous hydrogels are normally very loose after swelling and, when a small amount of pressure is applied, easily break apart. Some hydrogels have also been prepared that have reasonable mechanical properties, such as strength, ruggedness, and resiliency. However, very strong superporous hydrogels absorb limited amounts of water and thus have undesirable swelling properties. A preparation method for producing a hydrogel with both adequate swelling and mechanical properties is still lacking in the art.

SUMMARY OF THE INVENTION

This invention features a method for the preparation of a superporous hydrogel (SPH) in which its resulting physical and mechanical properties can be controlled by using a relatively simple ion-equilibration process, thereby producing a highly absorbent, yet structurally rugged and resilient, superporous hydrogel.

In a first aspect, the invention features a method of forming a hydrogel that includes the steps of, a) combining at least one ethylenically-unsaturated monomer, a cross-linking agent, and an ionic polysaccharide to form a mixture, b) subjecting the mixture to polymerization conditions to form a hydrogel, and c) reacting the hydrogel with one or more cations under equilibrating conditions, where at least one cation is used that was not used in step a) or, if the same mixture of cations is used in steps a) and c), the ratio of cations used in these steps is different. Preferably, the hydrogel that is formed by this method is a superporous hydrogel.

In one embodiment, the mixture includes one or more members of the group consisting of: a diluent, a foam stabilizer, a foaming aid, a reductant, an oxidant, and a blowing agent. Preferably, the mixture includes all of the members of this group.

In another embodiment, at least one of the cations used in step a) is monovalent and at least one of the cations used in step c) is divalent. Preferably the monovalent cations include $Na^+$, $K^+$, or $NH_4^+$ while divalent cations include $Ca^{2+}$, $Mg^{2+}$, $Ba^{2+}$, $Cu^{2+}$, $Zn^{2+}$, $Mn^{2+}$, or $Fe^{2+}$.

In yet another embodiment, the method includes an additional step of reacting the superporous hydrogel (SPH) formed in step c) with one or more cations under equilibrating conditions where at least one cation is used that was not used in step c), or if the same mixture of cations is used as in step c), the ratio of cations used in this additional step is different. Preferably, the additional step includes reaction of the hydrogel with $Ca^{2+}$, $Cu^{2+}$, $Zn^{2+}$, $Ba^{2+}$, $Mg^{2+}$, $Mn^{2+}$, $Fe^{2+}$, $Fe^{3+}$, $Cr^{3+}$, $Al^{3+}$, or $Ce^{4+}$. Most preferably, at least one of the cations reacted with said superporous hydrogel (SPH) formed in step c) has a valency of three or higher.

The polysaccharide of the invention can be, for example, salts of carboxymethylcellulose, alginate, hyaluronic acid, starch glycolate, carboxymethyl starch, dextran sulfate, pectinate, xanthan, carrageenan and chitosan. Preferably, the polysaccharide includes sodium salt of carboxymethylcellulose.

The ethylenically-unsaturated monomer of the invention can be, for example, (meth)acrylamide, N-isopropylacrylamide (NIPAM), N-cyclopropylacrylamide, diallyldimethylammonium chloride (DADMAC), 2-methacryloloxyethyl trimethylammonium chloride, N,N-dimethylaminoethyl acrylate, 2-hydroxyethyl acrylate (HEA), 2-hydroxyethyl methacrylate (HEMA), 2-hydroxypropyl methacrylate (HPMA), N-vinyl pyrrolidone (VP), (meth)acrylic acid (AA), salts of (meth)acrylic acid, salts and acids of esters of (meth)acrylic acid, amides of (meth)acrylic acid, N-alkyl amides of (meth)acrylic acid, salts and acids of N-alkyl amides of (meth)acrylic acid, itaconic acid, 2-acrylamido-2-methyl-1-propanesulfonic acid (AMPS), 3-sulfopropyl acrylate potassium salt (SPAK), 3-sulfopropyl methacrylate potassium salt or 2-(acryloyloxy)ethyltrimethyl-ammonium methyl sulfate (ATMS). Preferably, the mixture used in the formation of the hydrogel includes 2-hydroxyethyl acrylate as the ethylenically-unsaturated monomer.

The crosslinking agent of the invention can be, e.g., N,N'-methylenebisacrylamide, N, N'-ethylenebisacrylamide, poly(ethylene glycol) di(meth)acrylate, ethylene glycol di(meth)acrylate, ethyleneglycol diglycidyl ether, glycidyl methacrylate, polyamidoamine epichlorohydrin resin, trimethylolpropane triacrylate (TMPTA), piperazine diacrylamide, glutaraldehyde, epichlorohydrin, a crosslinking agent that includes one or more 1,2-diol structures, a crosslinking agent that includes one or more functionalized peptides, or a crosslinking agent that includes one or more functionalized proteins. Preferably, the mixture used in the formation of the hydrogel includes poly(ethylene glycol) diacrylate as the crosslinking agent.

In a second aspect, the invention features a method of dehydrating a hydrogel, preferably a superporous hydrogel, by lyophilization, such that a water/SPH weight to weight ratio of from 0.005 to 0.1 is achieved. In one embodiment, the dehydrating method includes the steps of, a) freezing the superporous hydrogel to about −10° C., with a cooling rate of about 3° C. per hour, b) maintaining the superporous hydrogel at about −10° C. for 16 to 24 hours, c) lyophilizing the superporous hydrogel at about −10° C. and at less than about 0.2 Torr for 60 to 80 hours, d) increasing the superporous hydrogel temperature to 10° C. at a rate of about 3° C. per hour, and e) maintaining the superporous hydrogel at 10° C. and at less than about 200 mTorr for at least 12 hours. In another embodiment of this aspect, the superporous hydrogel is prepared by a method of the present invention.

In a related aspect, the invention features a method for the dehydration of a hydrogel, preferably a superporous hydrogel, such that a water/SPH weight to weight ratio of from 0.005 to 0.1 is achieved, where the method includes the steps of, a) displacing water contained in the hydrogel with a non-aqueous, water-miscible solvent or solvent mixture, and b) removal of said non-aqueous solvent or solvent mixture at a pressure of less than 50 Torr or by heat. In one embodiment, the non-aqueous solvent can be, e.g., methanol, ethanol, 1-propanol, 2-propanol, tetrahydrofuran, dioxane, formic acid, acetic acid, acetonitrile, nitromethane, acetone, or 2-butanone. Preferably, the non-aqueous solvent includes ethanol. In another embodiment, the superporous hydrogel is prepared by a method of the present invention.

A dehydrated superporous hydrogel of the invention can include a medicament, a nutritional substance, or a fertilizer and be in the form of a film, a sheet, a particle, a granule, a fiber, a rod, or a tube. Preferably, the dehydrated hydrogel additionally includes a controlled release system for any of these substances.

By "crosslinking agent" is meant a molecule able to form a chemical bond to another substrate in the formation of a matrix.

By "monosaccharides" are meant polyhydric alcohols from three to ten or more carbon atoms containing either an aldehyde group (e.g., aldoses) or a keto group (e.g., ketoses), or masked aldehyde or keto groups, or derivatives thereof. Examples of monosaccharide units are the D and L configurations of glyceraldehyde, erythrose, threose, ribose, arabinose, xylose, lyxose, allose, altrose, glucose, mannose, gulose, idose, galactose, talose, dihydroxyacetone, erythrulose, ribulose, xylulose, puscose, fructose, sorbose and/or tagatose. Examples of monosaccharides also include those monosaccharide deoxy sugars, such as, for example, fucose, rhamnose, and digitoxose; deoxyamino sugars such as, for example, glucosamine, mannosamine, galactosamine; deoxyacylamino sugars such as, for example, N-acetylglucosamine, N-acetylmannosamine, and N-acetylgalactosamine; and aldonic, aldaric and/or uronic acids such as, for example, gluconic acid or glucuronic acid. Monosaccharides also include ascorbic acid, amino acid-carrying monosaccharides and monosaccharides which carry lipid, phosphatidyl or polyol residues.

By "peptide" is meant a molecule that contains from 2 to 100 natural or unnatural amino acid residues joined by amide bonds formed between a carboxyl group of one amino acid and an amino group from the next one. When referring to a crosslinking agent, the term "functionalized peptide" refers to those peptides that have at least two groups suitable for carrying out a crosslinking reaction. These groups include olefins, carbonyls, esters, acyl halides, alkyl halides, and the like.

By "protein" is meant a molecule that contains greater than 100 natural or unnatural amino acid residues joined by amide bonds formed from a carboxyl group of one amino acid and an amino group from the next one. When referring to a crosslinking agent, the term "functionalized protein" refers to those proteins that have at least two groups suitable for carrying out a crosslinking reaction. These groups include olefins, carbonyls, esters, acyl halides, alkyl halides, and the like.

The term "polysaccharide" is meant to include any polymer of monosaccharides, or mixtures of polymers of monosaccharides, or salts therein, and includes disaccharides, oligosaccharides, etc. Polysaccharides include starch, carrageenan, xanthan, dextran, cellulose, chitosan, glycogen, hyaluronic acid, alginic acid, pectin and glycosylaminoglycans. The polysaccharide of this invention may be unmodified or modified and the term polysaccharide is used herein to include both types. By modified polysaccharide it is meant that the polysaccharide can be derivatized or modified by typical processes known in the art, e.g., esterification, etherification, grafting, oxidation, acid hydrolysis, cross-linking and/or enzyme conversion. Typically, modified polysaccharides include esters such as the acetate and the half-esters of dicarboxylic acids, particularly the alkenylsuccinic acids; ethers, such as hydroxyethyl and hydroxypropyl starches and starches reacted with hydrophobic cationic epoxides; starches oxidized with hypochlorite; starches reacted with cross-linking agents such as phosphorous oxychloride, epichlorohydrin or phosphate derivatives prepared by reaction with sodium or potassium orthophosphate or tripolyphosphate and combinations thereof. These and other conventional modifications of starch are described in publications such as Starch: Chemistry and Technology, 2nd Edition, Ed. Whistler, BeMiller, and Paschall, Academic Press, 1984, Chapter X.

By "hydrogel" is meant a crosslinked polymer network that is not soluble in water but swells to an equilibrium size in the presence of water.

By "superporous hydrogel" is meant a hydrogel that has interconnecting pores.

DETAILED DESCRIPTION

To prepare a superporous hydrogel of the invention, an ethylenically-unsaturated monomer is mixed with several ingredients, including a crosslinker and a certain amount of an ionic polysaccharide, in a polymerization reaction. The mixture can also include one or more co-monomers, diluents, surfactants, foaming aids, initiators, and blowing agents. The mixture can be polymerized by any method known to those skilled in the art, as described by Odian in *Principles of Polymerization*, 3$^{rd}$ *Edition* (1991), Wiley-Interscience. Polymerization techniques can include, for example, solution, suspension, microsuspension, inverse suspension, dispersion, emulsion, microemulsion, and inverse emulsion polymerization.

The ethylenically-unsaturated monomer used to make the superporous hydrogel of the invention can be (meth)acrylic acid, salts of (meth)acrylic acid, esters of (meth)acrylic acid, salts and acids of esters of (meth)acrylic acid, amides of (meth)acrylic acid, N-alkyl amides (meth)acrylic acid, salts and acids of N-alkyl amides of (meth)acrylic acid, N-vinyl pyrrolidone, acrylamide, acrylamide derivatives (e.g., N-1-propylacrylamide, N-isopropylacrylamide), methacrylamide, methacrylamide derivatives (e.g., N-cyclopropylmethacrylamide), and the like, and mixtures thereof. Preferred monomers include acrylamide (AM), N-isopropylacrylamide (NIPAM), 2-hydroxyethyl acrylate (HEA), 2-hydroxyethyl methacrylate (HEMA), 2-hydroxypropyl methacrylate (HPMA), N-vinyl pyrrolidone (VP), acrylic acid (AA), sodium acrylate (Na+AA), potassium acrylate ($K^+AA$), ammonium acrylate ($NH_4^+AA$), methacrylic acid and its salts, N, N-dimethylaminoethyl acrylate, diallyldimethylammonium chloride (DADMAC), 2-acrylamido-2-methyl-1-propanesulfonic acid (AMPS), 3-sulfopropyl acrylate, potassium salt (SPAK), 3-sulfopropyl methacrylate, potassium salt (SPMAK), 2-(acryloyloxy)ethyltrimethylammonium methyl sulfate (ATMS), inorganic salts thereof, or mixtures thereof. Preferably, the concentration of monomer is from about 5% to about 50% (v/v) of the total reaction mixture volume when used as the primary monomer and from about 0.5% to about 10% (v/v) of the total reaction mixture volume when used as a secondary co-monomer. Most preferably, the reaction mixture includes 2-hydroxyethyl acrylate (HEA) as a primary monomer and a 50% (w/w) aqueous solution of 3-sulfopropyl acrylate, potassium salt as a co-monomer in a 4:1 (v/v) ratio, respectively, the combined volume of the two accounting for about 23% (v/v) of the total reaction mixture volume.

Crosslinking agents can be glutaraldehyde, epichlorohydrin, and degradable crosslinking agents including crosslinkers containing 1,2-diol structures (e.g., N,N'-diallyltartardiamide and ethylene glycol dimethacrylate), functionalized peptides and proteins (e.g., albumin modified with vinyl groups), ethylene glycol di(meth)acrylate, trimethylolpropane triacrylate (TMPTA), N,N'-methylenebisacrylamide (BIS), and piperazine diacrylamide. Multiolefinic crosslinking agents containing at least two vinyl groups, such as ethylene glycol di(meth)acrylate, poly (ethylene glycol) di(meth)acrylate, trimethylolpropane triacrylate (TMPTA), N,N'-methylenebisacrylamide (BIS), piperazine diacrylamide, crosslinkers containing 1,2-diol structures and two vinyl groups (e.g., N,N'-diallyltartardiamide or ethylene glycol dimethacrylate) are preferred. A most preferred crosslinking agent is poly(ethylene glycol) diacrylate. Preferably, the (v/v) ratio of crosslinker to monomer is from about 0.01/100 to about 1/10. Most preferably, the (v/v) ratio of crosslinker to monomer is from about 1/100 to 1/10.

In the preparation of the hydrogel, foam stabilization can be accomplished by physical or chemical means. For example, a rapid cooling or hot drying (for example, flash drying at a high temperature under an inert atmosphere) process can be used to stabilize the foam that has been produced by a gas blowing technique. Desirably, a surfactant can be used to stabilize the foam until the beginning of the gelling process. Useful surfactants include Triton surfactants, Tween and Span surfactants, Pluronic® surfactants (poly(ethylene oxide)-poly(propylene oxide)-poly(ethylene oxide) tri-block copolymers) (BASF), Silwet® surfactants (OSi Specialties Inc.), sodium dodecyl sulfate (Bio-Rad Laboratories), albumin (Sigma Chemical Company), gelatin, or combinations thereof. Preferably, Pluronic® F127 (PF127) is used. Surfactant concentrations in the range of about 0.2% to about 2% (w/v) of the total solution were found to be adequate. Preferably, the surfactant concentration is in the range of about 0.4% to about 1% (w/v). Most preferably, the surfactant concentration is about 0.7% (w/v)

Any gas blowing technique, for example, chemical or mechanical, can be used to prepare the superporous hydrogels of the invention. Because of the foaming technique used in the preparation of these hydrogels, they may also be called hydrogel foams. In the synthesis of a superporous hydrogel by a gas blowing technique, foaming and polymerization have to occur simultaneously, making it important to control the timing of these reactions. Inorganic carbonates, such as sodium carbonate, potassium carbonate, potassium bicarbonate, or, most preferably, sodium bicarbonate, can be used as a blowing agent. For the large-scale production of a superporous hydrogel, mechanical blowing through one or more atomizers is a satisfactory alternative to the chemical blowing method, since the heat generated during polymerization may not be dissipated quickly. Thus, a smaller amount of initiator may be used to delay the gelling time (e.g., more than 10 minutes) and, since mechanical blowing can start at any time for any duration, the foaming process may be initiated at the desired time with the foam height maintained as necessary.

Polymerization may be initiated by any polymerization-initiator system which is suitable for the polymerization of unsaturated monomers in the homogeneous or heterogeneous phase. In general terms, initiator systems that may be used in the process according to the present invention are those known to the person skilled in the art of polymer chemistry. Without restricting the present invention, such initiators are preferably free-radical or free-radical forming compounds or mixtures of substances, such as for example hydroperoxides, preferably cumyl hydroperoxide or tert.-butyl hydroperoxide, organic peroxides, preferably dibenzoyl peroxide, dilauryl peroxide, dicumyl peroxide, di-tert.-butyl peroxide, methyl ethyl ketone peroxide, tert.-butylbenzoyl peroxide, diisopropyl peroxydicarbonate, dicyclohexyl peroxydicarbonate, di-tert.-butyl peroxalate, inorganic peroxides, preferably potassium persulfate, potassium peroxydisulfate or hydrogen peroxide, azo compounds, preferably azobis(isobutyronitrile), 1,1'-azobis(1-cyclohexane nitrile), 4,4'-azobis(4-cyanovaleric acid) or triphenylmethylazobenzene, redox systems, preferably mixtures of peroxides and amines, mixtures of peroxides and reducing agents, optionally in the presence of metal salts and/or chelating agents. The initiator systems can be pure or in the form of mixtures of two, three or more different initiator systems. In another example, portions of the initiator system are added to the reaction separately in solid, liquid or gaseous form. This procedure is particularly suitable for redox initiator systems. In the present invention, preferably a combination of an oxidant and a reductant (a redox pair) is used as an initiator. Most preferably, the redox pair of ammonium persulfate (APS) and N,N,N',N'-tetramethylethylenediamine (TEMED) is used.

The pore size of the superporous hydrogels prepared by the foaming technique is usually larger than 100 μm, and it can easily reach the millimeter range. Usually, the pores are so large that they are visible with the unaided eye.

The ionic polysaccharide used can be any polysaccharide that includes negatively/positively charged groups that can counter the positive/negative charge of a cation/anion. Ordinarily, a primary cation is initially provided with the ionic polysaccharide of the superporous hydrogel formulation, with the polysaccharide playing a critical role in the process of subsequent ion-equilibration(s). Preferably, the polysaccharide is chosen from the list that includes sodium carboxymethylcellulose, sodium starch glycolate, sodium carboxymethyl starch, dextran sulfate, chitosan, hyaluronic acid, xanthan, carrageenan, gellan, sodium alginate, and sodium pectinate. Most preferably, the polysaccharide is sodium carboxymethylcellulose. The ratio of polysaccharide to total solution can be in the range of 0.1–10% w/v. Preferably, the range is 0.2–5% w/v. Most preferably, the range is 0.2–1.5% w/v.

Ion equilibration is a process by which ion exchange happens within the substrate structure. The exchange process may take place between any kinds of ions of different valences (e.g., monovalent, divalent, trivalent or higher). For example, 2-valent cations within the substrate can partially be replaced by 3-valent cations or vice versa. When the process of ion-equilibration is completed, the product contains equilibrium amounts of two or more cations. The equilibration just described results in considerable change in substrate properties. For example, sodium salt of carboxymethylcellulose is soluble in water, while its calcium-treated derivative is water-insoluble. Therefore, a simple partial replacement of sodium with calcium cation makes the final polymer sparingly soluble or insoluble in water. The general process of dramatically changing the properties of a substrate based on ion-exchange can also be applied to a superporous hydrogel formulation of the invention.

A hydrogel substrate can originally contain ions or can be ionized after its formation. A salt, ionic monomer, an ionic polymer, or any other ionic ingredient can provide the original or primary cation. This original cation is called primary, since it has to be partially replaced by another cation, i.e. secondary. The equilibrium mixture of primary and secondary cations can also be equilibrated with the third cation, i.e. tertiary cation and so on. To achieve desirable hydrogel properties, the process of ion-equilibration can be repeated with a number of different cations. A simple salt, ionic monomer, ionic polymer or another ion source can provide the secondary or tertiary cation. The ion-equilibration process can take place in an aqueous or a mixed aqueous/alcoholic medium, where the ions can move with freedom.

After foaming and polymerization are completed, a polysaccharide-containing superporous hydrogel can be immediately placed into an aqueous or mixed aqueous/alcoholic solution that includes any 2-valent cation, 3-valent cation or mixture of 2-, 3- or higher-valent cations like cerium. Preferably, the two-valent cation is $Ca^{2+}$, $Ba^{2+}$, $Mg^{2+}$, $Cu^{2+}$, $Zn^{2+}$, $Mn^{2+}$, or $Fe^{2+}$. Most preferably, the 2-valent cation is $Ca^{2+}$. Normally, the ion-exchange process between monovalent and two-valent cations is rapid and swelling of the hydrogel occurs. Although the process of ion-equilibration is fast, to ensure that the ion-equilibration process has been completed, a treatment time in the range from 0.5 hour to 24 hours is recommended. To obtain additional desirable properties, the ion-equilibrated superporous hydrogel may be retreated with a solution that includes a tertiary cation. Preferably, the 3-valent cation is iron or aluminum. As before with the secondary cation equilibration, the superporous hydrogel is placed into medium that includes a trivalent cation and cation equilibration occurs rapidly. To ensure that ion-equilibration has been completed, the hydrogel is left in the solution for period of time, preferably from 0.5 hour to 24 hours. The ion-equilibrated hydrogel is then thoroughly washed with pure water, washed with a non-aqueous, water-miscible solvent, and dried out in an oven or in a vacuum oven.

Alternatively, the purified superporous hydrogel can be dried out in an oven/vacuum oven or by a lyophilization technique.

Examples of how the ion-equilibration process can considerably change the final physical and mechanical properties of the superporous hydrogel produced are shown in Table 1.

TABLE 1

Influence of Cations on Superporous Hydrogel properties

| | $Na^{+1(a)}$ | $Na^{+1}$ exchange with $Ca^{+2(b)}$ | $Na^{+1}$ exchange with $Al^{+3}$ or $Fe^{+3(c)}$ | $Na^{+1}/Ca^{+2}$ exchange with $Al^{+3(c)}$ or $Fe^{+3}$ |
|---|---|---|---|---|
| Swelling capacity in water | Very high | High | Low | Medium |
| Swelling rate in water | Very slow | Slow | Very fast | Fast |
| Hydrogel Strength | Very low | Low | Very high | High |
| Surface property | Very slippery | Slippery | Very rough | Rough |
| Handling | Very difficult | Difficult | Very easy | Easy |
| Gel consistency | Very loose | Loose | Very tough | Tough |

[a] Cation provided by the polysaccharide that is sodium salt of carboxymethylcellulose.
[b] Cation provided by hydrated calcium chloride.
[c] Cation provided by hydrated aluminum chloride or hydrated ferric chloride.

For dehydration of an ion-equilibrated superporous hydrogel using a non-aqueous solvent the method includes the steps of, a) displacing water contained in the hydrogel matrix with a non-aqueous, water-miscible solvent or solvent mixture through a series of washings, and b) removal of said non-aqueous solvent or solvent mixture at a pressure of less than 50 Torr or by heat. The non-aqueous solvent can include methanol, ethanol, 1-propanol, 2-propanol, tetrahydrofuran, dioxane, formic acid, acetic acid, acetonitrile, nitromethane, acetone, or 2-butanone. Preferably, the non-aqueous solvent includes ethanol. When dehydrating a superporous hydrogel by lyophilization, a preferred method includes the steps of, a) freezing the superporous hydrogel sample from about 23° C. to about –10° C. with a cooling rate of about 3° C. per hour, b) maintaining the sample at about –10° C. for 16 to 24 hours, c) lyophilizing the sample at about –10° C. and at less than about 0.2 Torr for 60 to 80 hours, d) increasing the sample temperature to 10° C. at a rate of about 3° C. per hour, and e) maintaining the sample at 10° C. and at less than about 200 mTorr for at least 12 hours.

The dehydrated superporous hydrogels of the present invention rapidly swell to a relatively large size when placed in contact with aqueous fluids, yet remain mechanically strong in their swollen state. Taking advantage of these properties, these hydrogels can be useful as drug delivery systems (DDSs), as described by Park, et al., in *Biodegradable Hydrogels for Drug Delivery*, 1993, Technomic Pub. Co. or in *Hydrogels and Biodegradable Polymers for Bioapplications* (*ACS Symposium Series*, 627), 1996, Eds., Ottenbrite, et al., American Chemical Society.

Many DDSs release pharmaceutical agents from specific locations in the body over specific periods of time. Without additional measures taken to retard its passage through the alimentary canal, there is usually a ten hour limit for the absorption through the lining of the small intestine of an orally administered drug. In addition, some drugs are preferentially absorbed in certain regions in the gastrointestinal tract (GI), with many preferentially absorbed in the upper GI. In these cases, it is desirable to prolong the residence of a DDS in the upper GI tract (gastric retention) to enhance drug absorbance. Other hydrogels have also been used for this purpose, such as those described by Park, et al., in U.S. Pat. No. 6,271,278, which is hereby incorporated by reference.

Drug delivery can involve implanting a controlled release system within a matrix of a dehydrated superporous hydrogel of the invention. This, in turn, would be contained in a capsule (e.g., a gelatin capsule) or similar housing system that can be eroded by the acidic conditions in the stomach. The gastric retention of superporous hydrogels is based on their fast swelling property. Once a superporous hydrogel of the invention is exposed to gastric fluid, it rapidly swells to its maximum swelling capacity, typically in less than ten minutes. For their use in humans, superporous hydrogels that swell to a diameter of greater than 2 cm at low pH conditions are desirable as they are then unable to pass through the pylorus sphincter, ensuring prolonged residence in the stomach and better absorption of the drug through the upper GI.

In addition to drug delivery, the hydrogels of the invention can have a variety of applications including, for example, tissue engineering, vascular surgery (e.g., angioplasty) and drainage (e.g., from the kidney). Devices prepared using hydrogels of the invention can include vascular grafts, stents, catheters, cannulas, plugs, constrictors, tissue scaffolds, and tissue or biological encapsulants, and the like.

They may be applied to any use which requires a porous hydrogel material, particularly with an open pore structure. For example, the materials are useful as matrices or scaffolds into which cells can migrate, the cells being compatible therein and growing to achieve their intended function, such as in tissue replacement, eventually replacing the matrix depending on its biodegradability. Furthermore, the materials can be used to provide matrices already bound to cells, which may then be surgically implanted into a body. Further, the materials can be used as wound healing matrix materials, as matrices for in vitro cell culture studies or uses similar thereto. The stable structure of the materials of the invention provides ideal cell culture conditions.

The materials of the invention may also have application in cell transplantation, including for hepatocytes (see, D. J. Mooney, P. M. Kaufmann, K. Sano, K. M. McNamara, J. P. Vacanti, and R. Langer, "Transplantation of hepatocytes using porous biodegradable sponges," *Transplantation Proceedings*, 1994, 26:3425–3426; D. J. Mooney, S. Park, P. M. Kaufmann, K. Sano, K. McNamara, J. P. Vacanti, and R. Langer, "Biodegradable sponges for hepatocyte transplantation," *Journal of biomedical Materials Research*, 1995, 29:959–965), chondrocytes and osteoblasts (see, S. L. Ishaug, M. J. Yaszemski, R. Biciog, A. G. Mikos; "Osteoblast Function on Synthetic Biodegradable Polymers", *J. of Biomed. Mat. Res.*, 1994, 28:1445–1453).

Smooth muscle cells may readily adhere to the material prepared according to the invention and create three-dimensional tissues especially if appropriate cell adhesion ligand are coupled to the hydrogel structure within these porous structures; thus, they provide a suitable environment for cell proliferation. In addition, these materials have potential to incorporate growth factors.

Another useful application for the hydrogels of the invention is for guided tissue regeneration (GTR). This application is based on the premise that progenitor cells responsible for tissue regeneration reside in the underlying healthy tissue and can be induced to migrate into a defect and regenerate the lost tissue. A critical feature of materials for GTR is the transport of cells into the material, a property which is dictated by the pore size distribution and pore continuity, i.e., interconnectivity. The material must allow the desired cells to invade the material while preventing access to other cell types.

Because of the absorbent properties of the hydrogels of the invention they are very suitable for use in absorbent articles, and especially disposable absorbent articles. By "absorbent article" herein is meant a consumer product which is capable of absorbing significant quantities of water and other fluids (i.e., liquids), like body fluids. Examples of absorbent articles include disposable diapers, sanitary napkins, incontinence pads, paper towels, facial tissues, and the like.

Hydrogels of the invention can also be useful for protecting, holding or transplanting growing plants in the form of seeds, seedlings, tubers, cuttings, nursery stock, roots, transplants and the like. These hydrogels can aid a growing plant, either alone or in combination with fertilizer, agricultural modified minerals, and the like uniformly dispersed throughout.

The following non-limiting examples are illustrative of the invention.

EXAMPLE 1

The Formation of a Hydroxyethylacrylate-based Superporous Hydrogel Using an Ion-equilibration Process (Multiple Ions of $Na^{+1}$, $Ca^{2+}$ and $Fe^{3+}$; Multiple Treatments)

All reaction mixture components in the following example were used in the amounts indicated in Table 2.

In a glass tube were placed, hydroxyethylacrylate, poly (ethylene glycol) diacrylate (as a 1:2 (v/v) solution in hydroxyethylacrylate), water, Pluronic® F127, SPAK and CMC solutions. The components were mixed well until homogeneity was achieved. The reaction mixture was placed on a shaker and continually mixed. Glacial acetic acid was added, followed by the addition of tetramethylethylenediamine and ammonium persulfate. After all ingredients were thoroughly mixed, sodium bicarbonate was well dispersed into the reaction mixture. The resulting mixture began foaming and simultaneous gelation and foaming resulted in a superporous hydrogel foam. The foam was removed from the tube and placed into an aqueous solution of calcium chloride (1:200 (w/v) of hexahydrated calcium chloride in distilled water). The suspension was incubated for 2 hrs. The calcium-treated superporous hydrogel was immersed into an aqueous ferric chloride solution (1:300 (w/v) of hexahydrated ferric chloride in distilled water). The suspension was incubated for another 2 hrs.

EXAMPLE 2

The Formation of a Hydroxyethylacrylate-based Superporous Hydrogel Using an Ion-equilibration Process (Multiple Ions of $Na^{+1}$, $Ca^{2+}$ and $Al^{3+}$; Single Treatment)

Similar to Example 1 except the foam was removed from the tube and placed into a mixture of an aqueous solution of hexahydrated calcium chloride (1:200 (w/v)) and hexahydrated aluminum chloride (0.5: 200 (w/v)). The suspension was incubated for 2 hrs.

EXAMPLE 3

The Formation of a Hydroxyethylacrylate-based Superporous Hydrogel Using an Ion-equilibration Process (Multiple Ions of $Na^{+1}$ and $Fe^{3+}$; Single Treatment)

Similar to Example 1 except the foam was removed from the tube and 5 placed into an ethanolic aqueous solution of hexahydrated ferric chloride (1:200 (w/v)). The ethanol/water ratio was 1/3 v/v. The suspension was incubated for 2 hrs.

TABLE 2

Reaction mixture components

| Ingredient | Acting as: | Amount | Applicable range |
|---|---|---|---|
| Hydroxyethylacrylate (HEA) | Monomer | 2000 µL | 2000 µL |
| Poly(ethylene glycol) diacrylate solution in HEA; 1:2 v/v | Crosslinker | 80 µL | 50–250 µL |
| De-ionized water | Diluent/Solvent | 2000 µL | 500–3000 µL |
| Pluronic ® F127, 10 wt % aqueous solution | Surfactant | 800 µL | 100–1000 µL |
| Glacial acetic acid | Foaming aid | 160 µL | 40–200 µL |
| Sulfopropylacrylate, Potassium salt, 50 wt % aqueous solution | Co-monomer | 500 µL | 0–3000 µL |
| Carboxymethylcellulose, Sodium salt, 2 wt % aqueous solution | Polysaccharide | 3000 µL | 500–7000 µL |
| Tetramethylethylenediamine, 40 v/v % aqeuous solution | Reductant | 200 µL | 80–400 µL |
| Ammonium persulfate, 20 wt % aqueous solution | Oxidant | 200 µL | 40–400 µL |
| Sodium bicarbonate | Blowing agent | 250 mg | 60–300 mg |

With each example, the ion-equilibrated superporous hydrogel was thoroughly washed with de-ionized water (100 mL, five to ten times) until all impurities were removed. The purified ion-equilibrated superporous hydrogel was then dehydrated by treating it with ethyl alcohol (100 mL, one to three times), followed by drying in an air-forced oven at 40° C. Alternatively, the purified ion-equilibrated superporous hydrogel may directly be dried out in an oven or vacuum oven. As another alternative, the purified ion-equilibrated superporous hydrogel can be freeze-dried using the following lyophilization schedule: a) freezing the superporous hydrogel from room temperature to −10° C., with a freezing rate of −3° C./hr., b) keeping the sample at a temperature of −10° C. for 24 hrs., d) lyophilizing at 10–100 mTorr for 72 hrs., e) raising the temperature to 10° C. at a rate of 3° C./hr., and f) drying at 10° C. for 24 hrs.

From the foregoing description, it will be apparent that variations and modifications may be made to the invention described herein to adopt it to various applications and conditions. Such embodiments are also within the scope of the following claims.

All publications mentioned in this specification are herein incorporated by reference to the same extent as if each independent publication or patent application was specifically and individually indicated to be incorporated by reference.

What is claimed is:

1. A method of forming a hydrogel, comprising the steps of:
    a) combining at least one ethylenically-unsaturated monomer, a cross-linking agent, and an ionic polysaccharide with one or more cations to form a mixture;
    b) subjecting said mixture to polymerization to form said hydrogel; and
    c) reacting said hydrogel with one or more cations under equilibrating conditions, wherein
        i) at least one cation is used that was not used in step a), or
        ii) if the same mixture of cations is used in steps a) and c), the ratio of cations used in said steps is different; and
    d) reacting the hydrogel formed in step c) with one or more cations under equilibrating conditions, wherein
        i) at least one cation is used that was not used in step c), or
        ii) if the same mixture of cations is used as in step c), the ratio of cations used in said step is different.

2. The method of claim 1, wherein said mixture comprises one or more members of the group that consists of: a diluent, a foam stabilizer, a foaming aid, a reductant, an oxidant, and a blowing agent.

3. The method of claim 2, wherein said mixture comprises a diluent, a foam stabilizer, a foaming aid, a reductant, an oxidant, and a blowing agent.

4. The method of claim 1, wherein said hydrogel is a superporous hydrogel.

5. The method of claim 1, wherein at least one of the cations used in step a) is monovalent and at least one of the said cations used in step c) is divalent.

6. The method of claim 1, wherein at least one of the cations reacted with said hydrogel formed in step c) or d) is trivalent.

7. The method of claim 1, wherein said polysaccharide is carboxymethylcellulose, alginate, hyaluronic acid, starch glycolate, carboxymethyl starch, dextran sulfate, pectinate, xanthan, carrageenan, or chitosan.

8. The method of claim 7, wherein said polysaccharide is sodium carboxymethylcellulose.

9. The method of claim 1, wherein said ethylenically-unsaturated monomer is acrylamide (AM), N-isopropylacrylamide (NIPAM), 2-hydroxyethyl acrylate (HEA), 2-hydroxyethyl methacrylate (HEMA), 2-hydroxypropyl methacrylate (HPMA), N-vinyl pyrrolidone (VP), acrylic acid (AA), sodium/ potassium/ ammonium salts of acrylic acid, methacrylic acid and its salts, N,N-dimethylaminoethyl acrylate, 2-acrylamido- 2-methyl-1-propanesulfonic acid (AMPS), potassium salt of 3-sulfopropyl acrylate (SPAK), potassium salt of 3-sulfopropyl methacrylate (SPMAK), or 2-(acryloyloxyethyl)trimethylammonium methyl sulfate (ATMS).

10. The method of claim 9, wherein the ethylenically-unsaturated monomer is 2-hydroxyethyl acrylate.

11. The method of claim 1, wherein the crosslinking agent is N,N'-methylenebisacrylamide, ethylene glycol di(meth)acrylate, poly(ethylene glycol) di(meth)acrylate, trimethylolpropane triacrylate (TMPTA), piperazine diacrylamide, glutaraldehyde, epichlorohydrin, a crosslinking agent comprising one or more 1,2-diol structures, a crosslinking agent comprising one or more functionalized peptides, or a crosslinking agent comprising one or more proteins.

12. The method of claim 11, wherein the crosslinking agent is poly(ethylene glycol) diacrylate.

13. The method of claim 1, wherein said one or more cations used in step c) is selected from $Na^+$, $K^+$, $NH_4^+$, $Ca^{2+}$, $Ba^{2+}$, $Mg^{2+}$, $Cu^{2+}$, $Zn^{2+}$, $Mn^{2+}$, $Fe^{2+}$, $Fe^{3+}$, $Al^{3+}$, $Cr^{3+}$, or $Ce^{4+}$.

14. The method of claim 1, wherein said one or more cations used in step d) is selected from $Ca^{2+}$, $Cu^{2+}$, $Zn^{2+}$, $Ba^{2+}$, $Mg^{2+}$, $Mn^{2+}$, $Fe^{2+}$, $Fe^{3+}$, $Cr^{3+}$, $Al^{3+}$, or $Ce^{4+}$.

* * * * *